(12) United States Patent
Haroun et al.

(10) Patent No.: US 11,958,847 B1
(45) Date of Patent: Apr. 16, 2024

(54) PYRAZOLIDINEDIONE DERIVATIVES AND THEIR USE AS PPAR-GAMMA INHIBITORS

(71) Applicant: KING FAISAL UNIVERSITY, Al-Ahsa (SA)

(72) Inventors: Michelyne Haroun, Al-Ahsa (SA); Christophe Tratrat, Al-Ahsa (SA)

(73) Assignee: KING FAISAL UNIVERSITY, Al-Ahsa (SA)

(*) Notice: Subject to any disclaimer, the term of this patent is extended or adjusted under 35 U.S.C. 154(b) by 0 days.

(21) Appl. No.: 18/218,982

(22) Filed: Jul. 6, 2023

Related U.S. Application Data

(62) Division of application No. 18/116,985, filed on Mar. 3, 2023, now Pat. No. 11,845,743.

(51) Int. Cl.
*C07D 417/12* (2006.01)
*A61P 3/10* (2006.01)

(52) U.S. Cl.
CPC .............. *C07D 417/12* (2013.01); *A61P 3/10* (2018.01)

(58) Field of Classification Search
CPC ................................. C07D 417/12; A61P 3/10
See application file for complete search history.

(56) References Cited

U.S. PATENT DOCUMENTS

2013/0158063 A1   6/2013   Brown et al.

OTHER PUBLICATIONS

Haroun, Michelyne, Medicinal Chemistry, 16(6), 2020, pp. 812-825.*
Cancer and Metastasis Reviews (1998), 17(1), 91-106.*
Science (1999), vol. 286, 531-537.*
Che, L., et al., "Feprazone Displays Antiadipogenesis and Antiobesity Capacities in in Vitro 3 T3-L1 Cells and in Vivo Mice," ACS Omega, 6: pp. 6674-6680 (Mar. 7, 2021).
Haround, M., "In Silico Design, Synthesis and Evaluation of Novel Series of Benzothiazole-Based Pyrazolidinediones as Potent Hypoglycemic Agents," Medicinal Chemistry 16(6): pp. 812-825 (2020).#.
C24H18FN3O4—PubChemCID 6148505 Sep. 15, 2005.
C29H26FN3O5_PubChemCID 126414175 Apr. 10, 2017.

* cited by examiner

*Primary Examiner* — Rebecca L Anderson
(74) *Attorney, Agent, or Firm* — Nath, Goldberg & Meyer; Richard C. Litman

(57) ABSTRACT

The pyrazolidinedione derivatives were found to possess blood glucose lowering properties. These compounds were designed as potential PPAR gamma inhibitors, an essential molecular target for clinically used antidiabetic drugs. Owing to their promising anti-hyperglycemic activity, these derivatives may find useful applications for the treatment and/or prevention of obesity, diabetes type II and I, hyperglycemia and other diseases where PPAR gamma is implicated such as cancer, atherosclerosis and hyperlipidemia.

4 Claims, No Drawings

PYRAZOLIDINEDIONE DERIVATIVES AND THEIR USE AS PPAR-GAMMA INHIBITORS

CROSS-REFERENCE TO RELATED APPLICATION

This application is a divisional of U.S. patent application Ser. No. 18/116,985, filed on Mar. 3, 2023, the contents of which are hereby incorporated by reference in their entirety.

BACKGROUND

1. Field

The disclosure of the present patent application relates to pyrazolidinedione derivatives, and particularly to pyrazolidinedione derivatives as PPAR gamma inhibitors for the treatment of obesity and/or type-2 diabetes.

2. Description of the Related Art

Nuclear receptors represent an important class of receptor targets for drug discovery. The peroxisome proliferator-activated receptors (PPARs) are ligand activated transcription factors that belong to the nuclear receptor superfamily and play very important roles in multiple physiological pathways. Three PPAR receptor subtypes with distinct tissue distributions, designated as PPARα, PPARγ and PPARβ/δ, have been identified. The PPARs coordinate pathways involved in glucose and lipid homeostasis (Willson M. T. et al. J Med Chem 43:527-550, 2000; Berger J. et al. Annu Rev Med 53:409-435, 2002). In addition, PPARγ and PPARβ/δ are involved in developmental and differentiation pathways and therefore play important roles in embryogenesis, inflammation, obesity, hyperglycemia, diabetes, and cancer (Zaveri, T. N. et al. Canc Biol Ther 8:1252-1261, 2009; Elikkottil, J. et al. Canc Biol Ther 8:1262-1264, 2009).

Thus, new PPAR inhibitors that can be used for such treatments are desired.

SUMMARY

The pyrazolidinedione derivatives as PPAR gamma inhibitors, in one embodiment, relate to a compound having the formula I:

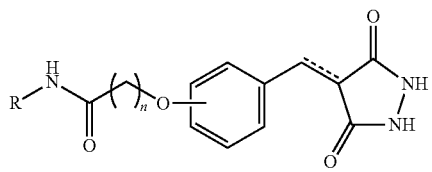

I or a pharmaceutically acceptable salt, ester, stereoisomer, or solvate thereof, wherein: ═══ represents a single or double bond; n is 1, 2, or 3; and R is an optionally substituted aryl, heteroaryl, arylalkyl, or heteroarylalkyl.

In another embodiment, the present subject matter relates to a compound having the formula I:

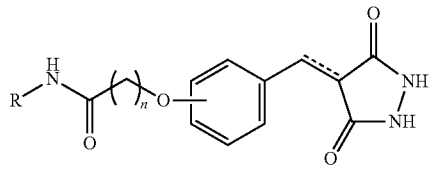

I or a pharmaceutically acceptable salt, ester, stereoisomer, or solvate thereof, wherein ═══ represents a single or double bond; n is 1, 2, or 3; and R is benzo[d]thiazole having one or two substituents independently selected from the group consisting of fluorine, chlorine, trifluoromethyl, trifluoromethoxy, methyl, and ethyl.

In a further embodiment, the present subject matter relates to a compound selected from the group consisting of N-(6-chlorobenzo[d]thiazol-2-yl)-2-(4-((3,5-dioxopyrazolidin-4-ylidene)methyl)phenoxy)acetamide (1); 2-(4-((3,5-dioxopyrazolidin-4-ylidene)methyl)phenoxy)-N-(6-(trifluoromethyl)benzo[d]thiazol-2-yl)acetamide (2); 2-(4-((3,5-dioxopyrazolidin-4-ylidene)methyl)phenoxy)-N-(6-(trifluoromethoxy) benzo[d]thiazol-2-yl)acetamide (3); N-(6-chloro-5-methylbenzo[d]thiazol-2-yl)-2-(4-((3,5-dioxopyrazolidin-4-ylidene)methyl)phenoxy)acetamide (4); N-(6-chloro-5-ethylbenzo[d]thiazol-2-yl)-2-(4-((3,5-dioxopyrazolidin-4-ylidene)methyl)phenoxy)acetamide (5); N-(6-chloro-7-methylbenzo[d]thiazol-2-yl)-2-(4-((3,5-dioxopyrazolidin-4-ylidene)methyl)phenoxy)acetamide (6); N-(4-chloro-6-fluorobenzo[d]thiazol-2-yl)-2-(4-((3,5-dioxopyrazolidin-4-ylidene)methyl)phenoxy)acetamide (7); N-(6-chlorobenzo[d]thiazol-2-yl)-3-(4-((3,5-dioxopyrazolidin-4-ylidene)methyl)phenoxy)propanamide (8); 3-(4-((3,5-dioxopyrazolidin-4-ylidene)methyl)phenoxy)-N-(6-(trifluoromethyl)benzo[d]thiazol-2-yl)propanamide (9); 3-(4-((3,5-dioxopyrazolidin-4-ylidene)methyl)phenoxy)-N-(6-(trifluoromethoxy)benzo[d]thiazol-2-yl)propanamide (10); N-(6-chloro-5-methylbenzo[d]thiazol-2-yl)-3-(4-((3,5-dioxopyrazolidin-4-ylidene)methyl)phenoxy)propanamide (11); N-(6-chloro-5-ethylbenzo[d]thiazol-2-yl)-3-(4-((3,5-dioxopyrazolidin-4-ylidene)methyl)phenoxy)propanamide (12); N-(6-chloro-7-methylbenzo[d]thiazol-2-yl)-3-(4-((3,5-dioxopyrazolidin-4-ylidene)methyl)phenoxy)propanamide (13); N-(4-chloro-6-fluorobenzo[d]thiazol-2-yl)-3-(4-((3,5-dioxopyrazolidin-4-ylidene)methyl)phenoxy)propanamide (14); and a pharmaceutically acceptable salt, ester, stereoisomer, or solvate thereof.

Further contemplated herein are pharmaceutical compositions containing these compounds, as well as methods of inhibiting PPAR-gamma and/preventing or treating a PPAR-mediated disease or condition by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., C6-24 aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S-0 bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), SiH$_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as an acute or chronic airway disorder or disease.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In one embodiment, the present subject matter relates to a compound having the formula I:

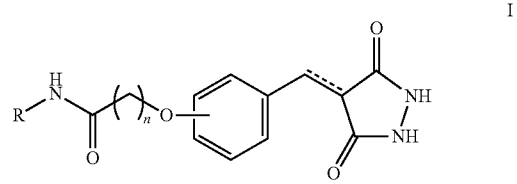

or a pharmaceutically acceptable salt, ester, stereoisomer, or solvate thereof, wherein: ═══ represents a single or double bond; n is 1, 2, or 3; and R is an optionally substituted aryl, heteroaryl, arylalkyl, or heteroarylalkyl.

In one embodiment, the present subject matter relates to a compound of formula I, wherein R is an optionally substituted benzo[d]thiazole.

In another embodiment, the present subject matter relates to a compound of formula I, wherein R has one or two substituents.

In a further embodiment, the present subject matter relates to a compound of formula I, wherein R has one or two substituents that are independently selected from the group consisting of halogen, trihalomethyl, trihalomethyloxy, and $C_1$-$C_6$ alkyl.

In yet another embodiment, the present subject matter relates to a compound of formula I, wherein R has one or two substituents that are independently selected from the group consisting of fluorine, chlorine, trifluoromethyl, trifluoromethoxy, methyl, and ethyl.

In another embodiment, the present subject matter relates to a compound of formula I, wherein the compound is selected from the group consisting of N-(6-chlorobenzo[d]thiazol-2-yl)-2-(4-((3,5-dioxopyrazolidin-4-ylidene)methyl)phenoxy)acetamide (1); 2-(4-((3,5-dioxopyrazolidin-4-ylidene)methyl)phenoxy)-N-(6-(trifluoromethyl)benzo[d]thiazol-2-yl)acetamide (2); 2-(4-((3,5-dioxopyrazolidin-4-ylidene)methyl)phenoxy)-N-(6-(trifluoromethoxy) benzo[d]thiazol-2-yl)acetamide (3); N-(6-chloro-5-methylbenzo[d]thiazol-2-yl)-2-(4-((3,5-dioxopyrazolidin-4-ylidene)methyl)phenoxy)acetamide (4); N-(6-chloro-5-ethylbenzo[d]thiazol-2-yl)-2-(4-((3,5-dioxopyrazolidin-4-ylidene)methyl)phenoxy)acetamide (5); N-(6-chloro-7-methylbenzo[d]thiazol-2-yl)-2-(4-((3,5-dioxopyrazolidin-4-ylidene)methyl)phenoxy)acetamide (6); N-(4-chloro-6-fluorobenzo[d]thiazol-2-yl)-2-(4-((3,5-dioxopyrazolidin-4-ylidene)methyl)phenoxy)acetamide (7); N-(6-chlorobenzo[d]thiazol-2-yl)-3-(4-((3,5-dioxopyrazolidin-4-ylidene)methyl)phenoxy)propan amide (8); 3-(4-((3,5-dioxopyrazolidin-4-ylidene)methyl)phenoxy)-N-(6-(trifluoromethyl)benzo[d]thiazol-2-yl)propanamide (9); 3-(4-((3,5-dioxopyrazolidin-4-ylidene)methyl)phenoxy)-N-(6-(trifluoromethoxy)benzo[d]thiazol-2-yl)propanamide (10); N-(6-chloro-5-methylbenzo[d]thiazol-2-yl)-3-(4-((3,5-dioxopyrazolidin-4-ylidene)methyl)phenoxy)propanamide (11); N-(6-chloro-5-ethylbenzo[d]thiazol-2-yl)-3-(4-((3,5-dioxopyrazolidin-4-ylidene)methyl)phenoxy)propanamide (12); N-(6-chloro-7-methylbenzo[d]thiazol-2-yl)-3-(4-((3,5-dioxopyrazolidin-4-ylidene)methyl)phenoxy)propanamide (13); N-(4-chloro-6-fluorobenzo[d]thiazol-2-yl)-3-(4-((3,5-dioxopyrazolidin-4-ylidene)methyl)phenoxy)propanamide (14); and a pharmaceutically acceptable salt, ester, stereoisomer, or solvate thereof.

Said differently, the present subject matter can relate to compounds of formula I selected from the group consisting of:

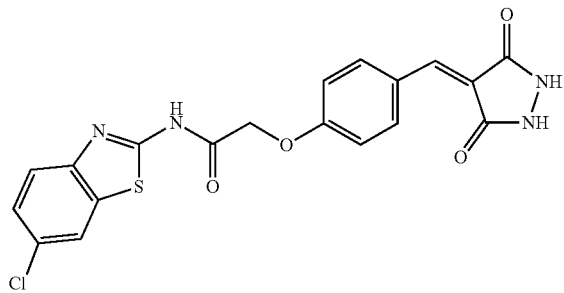

1

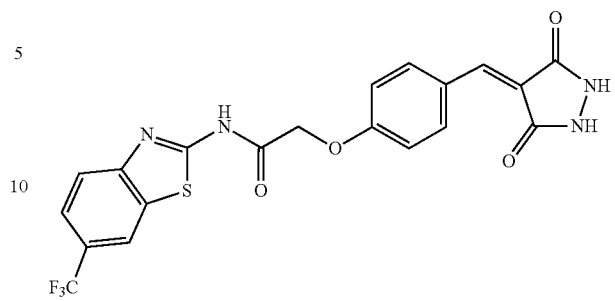

2

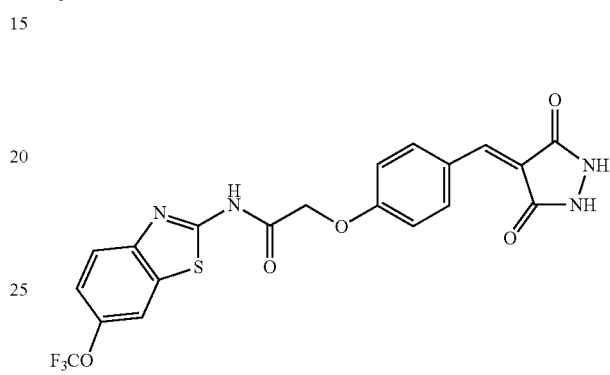

3

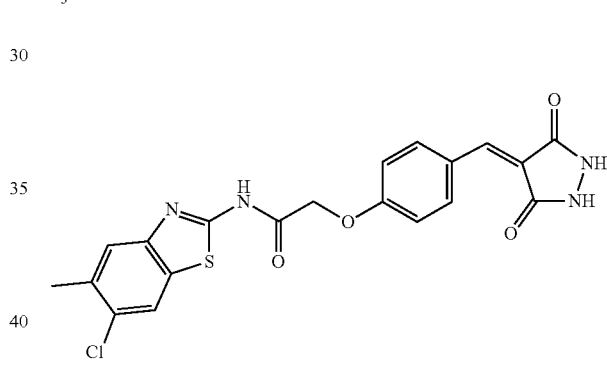

4

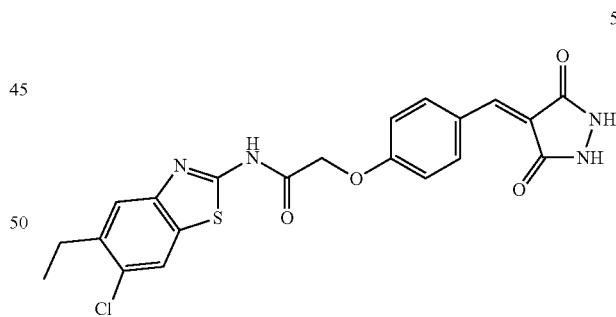

5

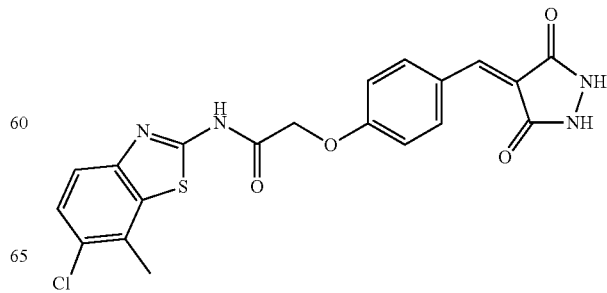

6 and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or the salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following reaction scheme:

Scheme 1

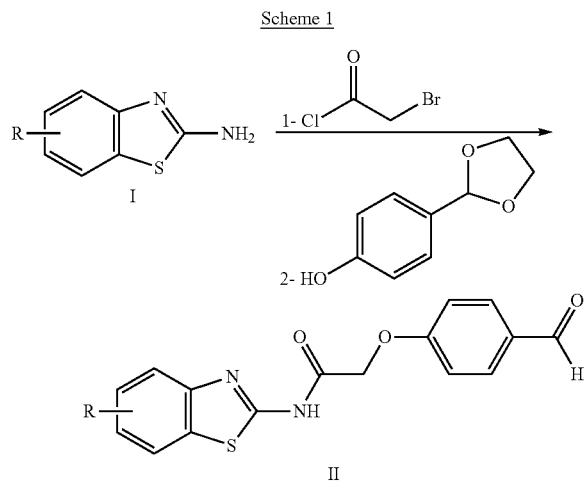

Procedure A: Preparation of N-(substitutedbenzo[d]thiazol-2-yl)-2-(4-formylphenoxy)acetamide II:

2-bromoacetyl chloride (0.05 mol) was added dropwise to an ice-cold solution of substituted 2-aminobenzo[d]thiazole derivatives I (0.05 mol), dimethylaminopyridine (0.075 mol DMAP), pyridine (5 mL) in dichloromethane (100 ml). The reaction mixture was stirred at room temperature for 2 hrs. After completion of reaction, the reaction mixture was washed with 10% HCl. The organic phase was separated and dried over $MgSO_4$, filtered and concentrated under reduced pressure. The obtained residue was diluted in THF (100 mL) and added to a cooled suspension of p-hydroxybenzaldehyde ethylene glycol acetal (0.05 mol) and LiH (0.05 mol) in THF (120 ml). The reaction mixture was refluxed until completion of reaction monitored by thin layer chromatography. After cooling, the reaction mixture was concentrated and treated with a cold brine solution to yield a precipitate which was filtered, washed with water and 10% NaOH solution. The solid residue was dissolved in 10% HCl then stirred at room temperature for 4 hours. When this solution was poured into ice cold water, a precipitate of benzaldehydes appeared, filtered and recrystallized to afford the N-(6-substituted benzo[d]thiazol-2-yl)-2-(4-formylphenoxy)acetamide II.

Scheme 2

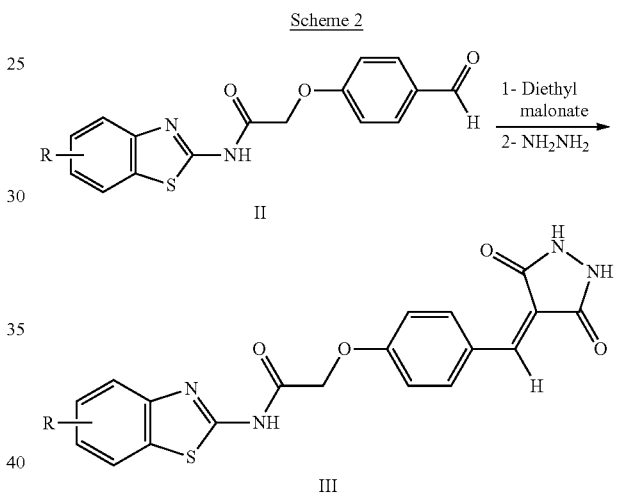

Procedure B: Preparation of N-(substitutedbenzo[d]thiazol-2-yl)-2-(4-((3,5-dioxopyrazolidin-4-ylidene)methyl)phenoxy)acetamide III To a solution of N-(substitutedbenzo[d]thiazol-2-yl)-2-(4-formylphenoxy)acetamide II (0.04 mol) and piperidine (0.06 mol) in THF (100 ml) was added dropwise diethyl malonate (0.042 mol) and was stirred under reflux for 3 hours. After concentration of the reaction mixture under reduced pressure, the residue obtained was dissolved in 100 ml of $CH_2Cl_2$ and washed with 3×50 ml of 10% HCl. The organic layer was separated, dried over anhydrous $MgSO_4$, filtered and then concentrated to yield the corresponding malonate derivative which were directly engaged in the next step without further purification. To a mixture of malonate (0.01 mole) and hydrazine hydrate (99%) (0.015 mole) in $CH_2Cl_2$ (40 ml) was heated at reflux for 4 hours. After cooling to room temperature, the solvent was removed under vacuum and the residue obtained was purified by silica gel column chromatography to afford the expected pyrazolidinedione derivatives III.

In another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

Non-limiting examples of suitable excipients, carriers, or vehicles useful herein include liquids such as water, saline, glycerol, polyethyleneglycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present compounds are typically administered at a therapeutically or pharmaceutically effective dosage, e.g., a dosage sufficient to provide treatment for an acute or chronic airway disease or disorder. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of a bacterial infection, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for foods or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrine derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium crosscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. In this regard, the present subject matter further relates to use of the present compounds for inhibiting PPAR-gamma in a patient. Similarly, the present subject matter relates to use of the present compounds for preventing or treating a PPAR-mediated disease or condition, especially obesity and/or diabetes.

In this regard, the present subject matter relates to a method of inhibiting PPAR-gamma in a patient, comprising administering to a patient in need thereof a therapeutically effective amount of a compound as described herein. Likewise, the present subject matter relates to a method of preventing or treating a PPAR-mediated disease or condition in a patient, comprising administering to a patient in need thereof a therapeutically effective amount of a compound as described herein.

In a further embodiment, the PPAR-mediated disease or condition can be selected from the group consisting of diabetes, obesity, hyperglycemia, metabolic syndrome, cancer, atherosclerosis, hyperlipidemia, and any combination thereof. Further in this regard, the diabetes can be type-I or type-II diabetes.

In one specific embodiment, the disease or condition can be obesity or diabetes.

The present subject matter also relates to the use of a compound as described herein in the manufacture of a pharmaceutical composition for the inhibition of PPAR-gamma, or for the prevention and/or treatment of a PPAR-mediated disease or condition, such as the diseases or conditions exemplified above. In particular, the present subject matter relates to the use of a compound as described herein in the manufacture of a pharmaceutical composition for the treatment or prophylaxis of a PPAR-mediated disease or condition, such as, but not limited to, diabetes, obesity, hyperglycemia, metabolic syndrome, cancer, atherosclerosis, hyperlipidemia. or any combination thereof.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In an embodiment, the present subject matter relates to a method of treating diabetes, obesity, hyperglycemia, metabolic syndrome, cancer, atherosclerosis, hyperlipidemia. or any combination thereof comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used.

The following examples relate to various methods of manufacturing certain specific compounds as described herein.

Example 1

N-(6-chlorobenzo[d]thiazol-2-yl)-2-(4-((3,5-dioxopyrazolidin-4-ylidene)methyl)phenoxy)acetamide (1)

Compound (1) was obtained according to the procedure described in Preparation A starting from 2-amino-6-chlorobenzo[d]thiazol followed by the procedure described in Preparation B. Elemental Analysis: Calculated C, 53.21; H, 3.06; N, 13.06. Found C, 53.14; H, 3.12; N, 12.98.

Example 2

2-(4-((3,5-dioxopyrazolidin-4-ylidene)methyl)phenoxy)-N-(6-(trifluoromethyl)benzo[d]thiazol-2-yl)acetamide (2)

Compound (2) was obtained according to the procedure described in Preparation A starting from 2-amino-6-(trifluoromethyl)benzo[d]thiazol followed by the procedure

Example 3

2-(4-((3,5-dioxopyrazolidin-4-ylidene)methyl)phenoxy)-N-(6-(trifluoromethoxy)benzo[d]thiazol-2-yl)acetamide (3)

Compound (3) was obtained according to the procedure described in Preparation A starting from 2-amino-6-(trifluoromethoxy)benzo[d]thiazol followed by the procedure described in Preparation B. Elemental Analysis: Calculated C, 50.21; H, 2.74; N, 11.71. Found C, 50.12; H, 2.67; N, 11.73.

Example 4

N-(6-chloro-5-methylbenzo[d]thiazol-2-yl)-2-(4-((3,5-dioxopyrazolidin-4-ylidene)methyl)phenoxy)acetamide (4)

Compound (4) was obtained according to the procedure described in Preparation A starting from 2-amino-6-chloro-5-methylbenzo[d]thiazol followed by the procedure described in Preparation B. Elemental Analysis: Calculated C, 54.24; H, 3.41; N, 12.65. Found C, 54.31; H, 3.34; N, 12.60.

Example 5

N-(6-chloro-5-ethylbenzo[d]thiazol-2-yl)-2-(4-((3,5-dioxopyrazolidin-4-ylidene)methyl)phenoxy)acetamide (5)

Compound (5) was obtained according to the procedure described in Preparation A starting from 2-amino-6-chloro-5-ethylbenzo[d]thiazol followed by the procedure described in Preparation B. Elemental Analysis: Calculated C, 55.20; H, 3.75; N, 12.26. Found C, 55.15; H, 3.71; N, 12.29.

Example 6

N-(6-chloro-7-methylbenzo[d]thiazol-2-yl)-2-(4-((3,5-dioxopyrazolidin-4-ylidene)methyl)phenoxy)acetamide (6)

Compound (6) was obtained according to the procedure described in Preparation A starting from 2-amino-6-chloro-7-methylbenzo[d]thiazol followed by the procedure described in Preparation B. Elemental Analysis: Calculated C, 54.24; H, 3.41; N, 12.65. Found C, 54.18; H, 3.36; N, 12.61.

Example 7

N-(4-chloro-6-fluorobenzo[d]thiazol-2-yl)-2-(4-((3,5-dioxopyrazolidin-4-ylidene)methyl)phenoxy)acetamide (7)

Compound (7) was obtained according to the procedure described in Preparation A starting from 2-amino-4-chloro-6-fluorobenzo[d]thiazol followed by the procedure described in Preparation B. Elemental Analysis: Calculated C, 51.07; H, 2.71; N, 12.54. Found C, 51.01; H, 2.64; N, 12.49.

Example 8

N-(6-chlorobenzo[d]thiazol-2-yl)-3-(4-((3,5-dioxopyrazolidin-4-ylidene)methyl)phenoxy)propanamide (8)

Compound (8) was obtained according to the procedure described in Preparation A starting from 2-amino-6-chlorobenzo[d]thiazol and 3-bromopropanoyl chloride instead of 2-bromoacetyl chloride followed by the procedure described in Preparation B. Elemental Analysis: Calculated C, 54.24; H, 3.41; N, 12.65. Found C, 54.17; H, 3.38; N, 12.60.

Example 9

3-(4-((3,5-dioxopyrazolidin-4-ylidene)methyl)phenoxy)-N-(6-(trifluoromethyl)benzo[d]thiazol-2-yl)propanamide (9)

Compound (9) was obtained according to the procedure described in Preparation A starting from 2-amino-6-(trifluoromethyl)benzo[d]thiazol and 3-bromopropanoyl chloride instead of 2-bromoacetyl chloride followed by the procedure described in Preparation B. Elemental Analysis: Calculated C, 52.94; H, 3.17; N, 11.76. Found C, 53.06; H, 3.08; N, 11.81.

Example 10

3-(4-((3,5-dioxopyrazolidin-4-ylidene)methyl)phenoxy)-N-(6-(trifluoromethoxy)benzo[d]thiazol-2-yl)propanamide (10)

Compound (10) was obtained according to the procedure described in Preparation A starting from 2-amino-6-(trifluoromethoxy)benzo[d]thiazol and 3-bromopropanoyl chloride instead of 2-bromoacetyl chloride followed by the procedure described in Preparation B. Elemental Analysis: Calculated C, 51.22; H, 3.07; N, 11.38. Found C, 51.29; H, 3.11; N, 11.33.

Example 11

N-(6-chloro-5-methylbenzo[d]thiazol-2-yl)-3-(4-((3,5-dioxopyrazolidin-4-ylidene)methyl)phenoxy)propanamide (11)

Compound (11) was obtained according to the procedure described in Preparation A starting from 2-amino-6-chloro-5-methylbenzo[d]thiazol and 3-bromopropanoyl chloride instead of 2-bromoacetyl chloride followed by the procedure described in Preparation B. Elemental Analysis: Calculated C, 55.20; H, 3.75; N, 12.26. Found C, 55.203 H, 3.71; N, 12.19.

Example 12

N-(6-chloro-5-ethylbenzo[d]thiazol-2-yl)-3-(4-((3,5-dioxopyrazolidin-4-ylidene)methyl)phenoxy)propanamide (12)

Compound (12) was obtained according to the procedure described in Preparation A starting from 2-amino-6-chloro-5-ethylbenzo[d]thiazol and 3-bromopropanoyl chloride instead of 2-bromoacetyl chloride followed by the procedure described in Preparation B. Elemental Analysis: Calculated C, 56.11; H, 4.07; N, 11.90. Found C, 56.03; H, 4.01; N, 11.82.

Example 1

N-(6-chloro-7-methylbenzo[d]thiazol-2-yl)-3-(4-((3,5-dioxopyrazolidin-4-ylidene)methyl)phenoxy)propanamide (13)

Compound (13) was obtained according to the procedure described in Preparation A starting from 2-amino-6-chloro-7-methylbenzo[d]thiazol and 3-bromopropanoyl chloride instead of 2-bromoacetyl chloride followed by the procedure described in Preparation B. Elemental Analysis: Calculated C, 55.20; H, 3.75; N, 12.26. Found C, 55.23; H, 3.64; N, 12.33.

Example 14

N-(4-chloro-6-fluorobenzo[d]thiazol-2-yl)-3-(4-((3,5-dioxopyrazolidin-4-ylidene)methyl)phenoxy)propanamide (14)

Compound (14) was obtained according to the procedure described in Preparation A starting from 2-amino-4-chloro-6-fluorobenzo[d]thiazol and 3-bromopropanoyl chloride instead of 2-bromoacetyl chloride followed by the procedure described in Preparation B. Elemental Analysis: Calculated C, 52.12; H, 3.06; N, 12.16. Found C, 52.18; H, 2.98; N, 12.04.

Example 10

Anti-Hyperglycemic Activity Evaluation

The following example relates to the anti-hyperglycemic effectiveness of certain specific compounds as described herein.

The antidiabetic activity of the derivatives 1-14 was assessed following Streptozotocin (STZ) model [Mariappan, G et al *J. Chem. Sci.,* 2011, 123(3), 335-341]. Diabetes was experimentally generated in albino rats by intraperitoneal injection of a solution of STZ (60 mg/kg) in sterile normal saline. Animals were considered diabetic after 3 days of injection of STZ and blood glucose range registered was 200-300 mg/dL. Rats were partitioned into 8 groups consisting of 6 rats in each group (n=6). The control group consisted of the first group of diabetic animals serving as vehicle control and treated orally with carboxymethylcellulose (CMC) (0.5%, 1 ml) alone; Group 2 of diabetic rats was treated with rosiglitazone 100 mg/kg. Compounds 1-14 were administered to groups (3-8) of diabetic rats in a unique oral dose enclosing 50 mg per body weight in Kg for 7 continuous days, respectively. Blood collections were operated by tail vein sampling. The measurements of blood glucose were performed at 0, 5 and 10 days interval. Bayer's Contour TS system was used in order to monitor blood glucose level. In overnight-fasted rats, fasting blood glucose level was measured in all the groups as a base line at 0 time. All blood glucose data were expressed as mean±SEM. The analysis of the data including the variance analysis (ANOVA) and all mean comparisons were accomplished by Tukey-Kramer method. Results are regarded as significant when P<0.01. The anti-hyperglycemic activity (AA) was presented as % AA and computed as follows: % AA=100×[blood glucose level (0-day)−blood glucose level (10-day)]/[blood glucose level (0-day)].

The blood glucose level and the calculated anti-hyperglycemic activity of the tested compounds 1-14 are listed in Table 1. All tested compounds were observed to significantly retain the glucose-lowering effect in in vivo model, demonstrating a percent anti-hyperglycemic activity in a range from 58.6% to 70.1% while the drug reference Rosiglitazone showed 62.0% of anti-hyperglycemic activity. The in-vivo results demonstrated that the present compounds possessed favorable anti-hyperglycemic activity and for many of them displayed greater anti-hyperglycemic activity to that of the drug control Rosiglitazone.

TABLE 1

Blood glucose level and % Anti-hyperglycemic activity of the tested compounds 1-14

| | Blood glucose level (mg/dl) | | | % Anti-hyperglycemic activity |
|---|---|---|---|---|
| | 0-day | 5-day | 10-day | |
| Control (0.5% CMC) | 346.5 ± 4.5 | 378.2 ± 5.1 | 416.2 ± 5.1 | |
| 1 | 339.4 ± 5.3 | 157.5 ± 3.7 | 123.9 ± 4.2 | 63.5 |
| 2 | 345.7 ± 4.7 | 163.7 ± 2.8 | 123.4 ± 3.5 | 64.3 |
| 3 | 349.6 ± 3.9 | 172.4 ± 3.4 | 141.6 ± 2.8 | 59.5 |
| 4 | 337.4 ± 4.2 | 160.2 ± 4.1 | 113.4 ± 2.6 | 66.4 |
| 5 | 341.8 ± 5.1 | 155.3 ± 3.9 | 127.1 ± 3.1 | 62.8 |
| 6 | 347.5 ± 5.6 | 161.3 ± 4.5 | 143.9 ± 5.3 | 58.6 |
| 7 | 341.8 ± 4.4 | 174.1 ± 4.2 | 115.2 ± 4.2 | 66.3 |
| 8 | 338.9 ± 4.8 | 166.5 ± 3.7 | 106.1 ± 5.1 | 68.7 |
| 9 | 352.4 ± 2.6 | 159.6 ± 4.6 | 105.4 ± 3.2 | 70.1 |
| 10 | 348.2 ± 3.7 | 153.2 ± 4.2 | 105.2 ± 4.7 | 69.8 |
| 11 | 338.5 ± 4.3 | 168.7 ± 3.4 | 107.0 ± 2.4 | 68.4 |
| 12 | 340.7 ± 5.1 | 171.6 ± 5.1 | 121.9 ± 3.6 | 64.2 |
| 13 | 344.9 ± 3.8 | 168.4 ± 4.3 | 119.1 ± 4.3 | 65.5 |
| 14 | 352.4 ± 4.0 | 162.5 ± 5.6 | 109.6 ± 5.4 | 68.9 |
| Rosiglitazone | 341.6 ± 4.7 | 162.1 ± 3.8 | 129.7 ± 3.7 | 62.0 |

Values are expressed as mean ± SEM: (n = 6),
*$P < 0.01$.

It is to be understood that the pyrazolidinedione derivatives as PPAR-gamma inhibitors are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:
1. A method of inhibiting PPAR-gamma in a patient, comprising administering to a patient in need thereof a therapeutically effective amount of a compound selected from the group consisting of:
  N-(6-chlorobenzo[d]thiazol-2-yl)-2-(4-((3,5-dioxopyrazolidin-4-ylidene)methyl) phenoxy)acetamide (1);
  2-(4-((3,5-dioxopyrazolidin-4-ylidene)methyl)phenoxy)-N-(6-(trifluoromethyl) benzo[d]thiazol-2-yl)acetamide (2);
  2-(4-((3,5-dioxopyrazolidin-4-ylidene)methyl)phenoxy)-N-(6-(trifluoromethoxy) benzo[d]thiazol-2-yl)acetamide (3);
  N-(6-chloro-5-methylbenzo[d]thiazol-2-yl)-2-(4-((3,5-dioxopyrazolidin-4-ylidene) methyl)phenoxy)acetamide (4);

N-(6-chloro-5-ethylbenzo[d]thiazol-2-yl)-2-(4-((3,5-dioxopyrazolidin-4-ylidene) methyl)phenoxy)acetamide (5);

N-(6-chloro-7-methylbenzo[d]thiazol-2-yl)-2-(4-((3,5-dioxopyrazolidin-4-ylidene) methyl)phenoxy)acetamide (6);

N-(4-chloro-6-fluorobenzo[d]thiazol-2-yl)-2-(4-((3,5-dioxopyrazolidin-4-ylidene) methyl)phenoxy)acetamide (7);

N-(6-chlorobenzo[d]thiazol-2-yl)-3-(4-((3,5-dioxopyrazolidin-4-ylidene) methyl)phenoxy)propanamide (8);

3-(4-((3,5-dioxopyrazolidin-4-ylidene)methyl)phenoxy)-N-(6-(trifluoromethyl) benzo[d]thiazol-2-yl)propanamide (9);

3-(4-((3,5-dioxopyrazolidin-4-ylidene)methyl)phenoxy)-N-(6-(trifluoromethoxy) benzo[d]thiazol-2-yl)propanamide (10);

N-(6-chloro-5-methylbenzo[d]thiazol-2-yl)-3-(4-((3,5-dioxopyrazolidin-4-ylidene) methyl)phenoxy)propanamide (11);

N-(6-chloro-5-ethylbenzo[d]thiazol-2-yl)-3-(4-((3,5-dioxopyrazolidin-4-ylidene) methyl)phenoxy)propanamide (12);

N-(6-chloro-7-methylbenzo[d]thiazol-2-yl)-3-(4-((3,5-dioxopyrazolidin-4-ylidene) methyl)phenoxy)propanamide (13);

N-(4-chloro-6-fluorobenzo[d]thiazol-2-yl)-3-(4-((3,5-dioxopyrazolidin-4-ylidene) methyl)phenoxy)propanamide (14);

and a pharmaceutically acceptable salt, ester, stereoisomer, or solvate thereof.

2. A method of treating a PPAR-mediated disease or condition in a patient, comprising administering to a patient in need thereof a therapeutically effective amount of a compound selected from the group consisting of:

N-(6-chlorobenzo[d]thiazol-2-yl)-2-(4-((3,5-dioxopyrazolidin-4-ylidene)methyl) phenoxy)acetamide (1);

2-(4-((3,5-dioxopyrazolidin-4-ylidene)methyl)phenoxy)-N-(6-(trifluoromethyl) benzo[d]thiazol-2-yl)acetamide (2);

2-(4-((3,5-dioxopyrazolidin-4-ylidene)methyl)phenoxy)-N-(6-(trifluoromethoxy) benzo[d]thiazol-2-yl)acetamide (3);

N-(6-chloro-5-methylbenzo[d]thiazol-2-yl)-2-(4-((3,5-dioxopyrazolidin-4-ylidene) methyl)phenoxy)acetamide (4);

N-(6-chloro-5-ethylbenzo[d]thiazol-2-yl)-2-(4-((3,5-dioxopyrazolidin-4-ylidene) methyl)phenoxy)acetamide (5);

N-(6-chloro-7-methylbenzo[d]thiazol-2-yl)-2-(4-((3,5-dioxopyrazolidin-4-ylidene) methyl)phenoxy)acetamide (6);

N-(4-chloro-6-fluorobenzo[d]thiazol-2-yl)-2-(4-((3,5-dioxopyrazolidin-4-ylidene) methyl)phenoxy)acetamide (7);

N-(6-chlorobenzo[d]thiazol-2-yl)-3-(4-((3,5-dioxopyrazolidin-4-ylidene) methyl)phenoxy)propanamide (8);

3-(4-((3,5-dioxopyrazolidin-4-ylidene)methyl)phenoxy)-N-(6-(trifluoromethyl) benzo[d]thiazol-2-yl)propanamide (9);

3-(4-((3,5-dioxopyrazolidin-4-ylidene)methyl)phenoxy)-N-(6-(trifluoromethoxy) benzo[d]thiazol-2-yl)propanamide (10);

N-(6-chloro-5-methylbenzo[d]thiazol-2-yl)-3-(4-((3,5-dioxopyrazolidin-4-ylidene) methyl)phenoxy)propanamide (11);

N-(6-chloro-5-ethylbenzo[d]thiazol-2-yl)-3-(4-((3,5-dioxopyrazolidin-4-ylidene) methyl)phenoxy)propanamide (12);

N-(6-chloro-7-methylbenzo[d]thiazol-2-yl)-3-(4-((3,5-dioxopyrazolidin-4-ylidene) methyl)phenoxy)propanamide (13);

N-(4-chloro-6-fluorobenzo[d]thiazol-2-yl)-3-(4-((3,5-dioxopyrazolidin-4-ylidene) methyl)phenoxy)propanamide (14);

and a pharmaceutically acceptable salt, ester, stereoisomer, or solvate thereof;

wherein the PPAR-mediated disease or condition is selected from the group consisting of diabetes, obesity, hyperglycemia, metabolic syndrome, atherosclerosis, and hyperlipidemia.

3. The method of claim 2, wherein the diabetes is type-I or type-II diabetes.

4. The method of claim 2, wherein the disease or condition is obesity or diabetes.

* * * * *